United States Patent [19]

Isa et al.

[11] 3,997,622

[45] Dec. 14, 1976

[54] METHOD FOR PREPARATION OF OLEFIN OLIGOMER

[75] Inventors: Hiroshi Isa; Toshiyuki Ukigai, both of Yachiyo; Anri Tominaga, Tokyo; Michito Sato, Yokohama, all of Japan

[73] Assignee: Lion Fat & Oil Co., Ltd., Tokyo, Japan

[22] Filed: Jan. 26, 1976

[21] Appl. No.: 652,426

[30] Foreign Application Priority Data

Jan. 30, 1975 Japan .............................. 50-11897

[52] U.S. Cl. ....................................... 260/683.15 B
[51] Int. Cl.$^2$ .......................................... C07C 3/18
[58] Field of Search .......... 260/683.15 R, 683.15 B

[56] References Cited

UNITED STATES PATENTS 2,569,383  9/1951  Leyonmark et al. ...... 260/683.15 B
3,952,071  4/1976  Ise et al. .................... 260/683.15 B

*Primary Examiner*—C. Davis
*Attorney, Agent, or Firm*—Woodhams, Blanchard and Flynn

[57] ABSTRACT

A method of preparing an olefin oligomer by polymerizing an olefin having more than 6 carbon atoms, wherein said olefin is to be polymerized in the presence of a catalyst consisting of (a) polyhydric alcohol derivatives obtained by substituting hydrogen atoms of all the whole hydroxyl groups of polyhydric alcohol by either acyl group exclusively or acyl group and alkyl groups, both said acyl group and alkyl group having 1 – 20 carbon atoms, (b) aluminum halide in an amount of 0.7 – 1.0 mole per each ester bond and ether bond possessed by said polyhydric alcohol derivative and (c) metallic aluminum powder.

5 Claims, No Drawings

METHOD FOR PREPARATION OF OLEFIN OLIGOMER

BACKGROUND OF THE INVENTION

The present invention relates to a method for preparation of olefin oligomers, and particularly relates to a method for preparation of olefin oligomers which can perfectly prevent halogen from getting mixed in the polymerization product and provide olefin oligomer having a low viscosity and a high viscosity index at a high yield.

As the well-known methods for polymerization of olefins, there are a method employing Lewis acid catalyst such as aluminum chloride, a method employing a mixture of aluminum chloride and metallic aluminum powder or metallic zinc powder as the catalyst, etc. There is also known a method of effecting polymerization by employing a liquid catalyst prepared by dissolving excess aluminum halide in a complex consisting of aluminum halide and ethyl acetate (molar ratio = 1:1) (cf. Japanese Pat. Publication No. 3804/1969). However, all of these methods are defective in that, they can produce no more than a polyolefin oil having a relatively high viscosity under the ordinary reaction conditions, and in the case where the reaction temperature is elevated with a view to preparing a low-viscosity polyolefin oil, not only the viscosity index of the resulting polyolefin oil will be reduced but also the yield thereof will decrease.

Another trouble with the conventional methods for polymerization of olefin lies in that the halogenous component of the catalyst would get mixed in the product polyolefin oils. The presence of halogen in the product has a bad influence of grave importance on the process of after-treatment of the polymerization product. For instance, at the time of distilling the monomer and/or dimer from the polymerization product, there takes place the thermal cracking of a part of the halogen in the polyolefin oil giving rise to hydrogen chloride, entailing such a trouble that the distillation apparatus gets corroded thereby. Furthermore, at the time of the hydrogenation of the double bond remaining in the polymerization product for the purpose of improving the heat stability as well as oxidation stability of said product, there occurs such a trouble that the hydrogenation catalyst would be turned to be inactive by the halogen.

Consequently, it is in fact impossible to prepare an olefin oligomer having low viscosity and high viscosity index and scarcely containing halogen mixed therein which is qualified for such uses as gas turbine oil, hydraulic fluids for aircraft, insulating oil, cosmeric base, etc.

Under such circumstances, U.S. Ser. No. 538,965 discloses a method of effecting polymerization of olefin having more than 6 carbon atoms in the presence of a mixture consisting of (a) polyhydric alcohol derivative selected from esters and ethers of polyhydric alcohol and aluminum halide. According to said method, it is possible to obtain an olefin oligomer having a viscosity (in terms of kinematic viscosity at 100° F) of as low as 15 – 45 centistokes and a viscosity index (VIE) of as high as 120–145 and scarcely containing halogen at the yield of about 75–85%.

The present invention aims at further improvement of the method for preparation of olefin oligomer disclosed in said previous invention, and particularly it proposes a method for preparation of olefin oligomer as an improvement of the previous invention by the present inventors from the viewpoints of both the yield of olefin oligomer and the prevention of halogen from getting mixed in the product olefin oligomer.

SUMMARY OF THE INVENTION

The method of preparing an olefin oligomer according to the present invention is characterized by the polymerization of an olefin having more than 6 carbon atoms in the presence of a catalyst consisting of (a) polyhydric alcohol derivative obtained by substituting hydrogen atoms of the whole hydroxyl groups of polyhydric alcohol by either acyl group exclusively or acyl group and alkyl group, both said acyl group and alkyl group having 1 – 20 carbon atoms, (b) aluminum halide in an amount of 0.7 – 1.0 mole per each ester bond and ether bond possessed by said polyhydric alcohol derivative and (c) metallic aluminum powder. According to this polymerization method, it is possible to obtain an olefin oligomer with low viscosity and high viscosity index equivalent to that in the previous invention — to be concrete, an olefin oligomer having a viscosity of 15 – 45 centistokes and a viscosity index of 120 – 145 and containing no halogen at all — at a high yield of more than 90%.

DETAILED DESCRIPTION OF THE INVENTION

The 'olefin oligomer containing no halogen at all' herein means an olefin oligomer having properties such that, when one and the same Raney nickel catalyst is repeatedly used for performing hydrogenation treatment 10 times, each of said hydrogenation treatments comprising the processes of subjecting said olefin oligomer to 3 hours' hydrogenation employing said Raney nickel catalyst in an amount of 3 wt.% relative to the olefin oligomer under the condition that 10 Kg/cm$^2$ in hydrogen pressure and 150° C in reaction temperature, separating the catalyst from the resulting hydrogenated oil thereafter and reusing the thus separated catalyst for the next hydrogenation treatment to be performed under the same condition as above, the bromine number of the hydrogenated oil obtained through the tenth hydrogenation treatment is less than 0.5. In this connection, in the case where any halogen is contained in the olefin oligomer, deterioration of the catalyst is remarkable at the time of the hydrogenation treatment and the catalytic efficiency thereof lowers, so that it is infeasible to obtain a hydrogenated oil having the bromine number of less than 0.5 in said tenth hydrogenation treatment.

It is further added for precaution's sake that in the present invention the measurement of the halogen content in the olefin oligomer has been conducted by an indirect means as above for there is available no opposite method of directly measuring said content at present.

The essential feature of the present invention lies in the polymerization catalyst employed therein. As stated in the foregoing, the catalyst for use in the present invention is composed of three ingredients, namely, polyhydric alcohol derivative, aluminum halide and metallic aluminum powder. Of these ingredients, said polyhydric alcohol derivative means esters of polyhydric alcohol to be obtained by substituting hydrogen atoms of the whole hydroxyl groups of polyhydric alcohol by either acyl group exclusively or acyl group and alkyl group, both of said acyl group and alkyl group having 1 – 20 carbon atoms. To be concrete, the polyhydric alcohol derivative for use in the present invention includes ethoxyethyl acetate, butoxypropyl acetate, ethoxyethoxyethyl acetate, methoxyethoxyethyl propionate, 4-methoxylbutyl caproate, lauroxyethyl octanate, ethylene glycol diacetate, ethylene glycol dicaproate, propylene glycol dipropionate, 1,3-diacetoxypropane, 1,4-diacetoxybutane, trans-1,4-diacetoxybutene, 1,5-diacetoxypentane, diethylene glycol diacetate, dibutylene glycol dipropionate, triethylene glycol didecanate, pentaerythritol tetraacetate, etc. And, especially when ethoxyethyl acetate, butoxypropyl acetate, ethoxyethoxyethyl acetate, ethylene glycol diacetate, 1,3-diacetoxypropane or 1,4-diacetoxybutane among these polyhydric alcohol derivatives is applied, there is generally obtained a satisfactory result.

In the polymerization method according to the present invention, the presence of aluminum halide in an amount of 0.7 – 1.0 mole per 1 ester bond and ether bond possessed by said polyhydric alcohol derivative is required; in the case where the amount of the aluminum halide is less than this, the yield of the resulting olefin oligomer decreases, while in the case where it is more than this, the viscosity of same increases. Therefore, in the present invention, it is essential to set the amount of the aluminum halide to be mixed with the polyhydric alcohol derivative in the foregoing range, and on this occasion, the appropriate amount of the aluminum halide is in the range of 0.1 – 5 mol.% — preferably in the range of 1.0 – 3.0 mol.% — relative to the material olefin. The applicable aluminum halide can be illustrated by aluminum fluoride, aluminum chloride, aluminum bromide and aluminum iodide, among which aluminum chloride is most desirable.

In the polymerization catalyst for use in the present invention, metallic aluminum powder is also to be present. The appropriate amount of said metallic aluminum powder to be present on this occasion is in the range of 2.7 – 135 g per 1 mole of aluminum halide; in the case where the amount of the metallic aluminum powder is short of this range, it is impossible to obtain an olefin oligomer not containing halogen, while application of the metallic aluminum powder in an amount exceeding this range — though it is permissible — will scarcely bring on any substantial furtherance of the effect.

In the polymerization method according to the present invention, an olefin having more than 6 carbon atoms is to be polymerized in the presence of the above described catalyst composed of polyhydric alcohol derivative, aluminum halide and metallic aluminum powder. As to the material olefin, either of α-olefin and internal olefin is applicable, and to be concrete, hexane-1, octene-1, decene-1, 2-ethyl octene-1, tridecene-3, octadecene-2, etc. are illustrative of the applicable olefin. Also, mixtures of these olefins are of course applicable as the material olefin.

As to the reaction temperature, strictly speaking, it varies with the kind of the polyhydric alcohol derivative as well as aluminum halide employed, coupled with the relative volume ratio of these two ingredients to the metallic aluminum powder, but it is usually in the range of 50° – 150° C. And, as the general tendency, in the case where the reaction temperature is too low, halogen tends to get mixed in the product polyolefin oil, while in the case where it is too high, the viscosity index of the product polyolefin oil tends to become low. As to the pressure for reaction, atmospheric pressure is usually applied, but it is of course possible to effect the reaction under elevated pressure.

As to the procedure for effecting the reaction, it is a common procedure to mix the aluminum halide together with the metallic aluminum powder in the polyhydric alcohol derivative and then add the material olefin to the resulting solution thereby to effect polymerization, but it also will do to prepare a catalyst according to the present invention beforehand by employing an appropriate inactive solvent and then add the material olefin thereto.

The polymerization method of the present invention can be practiced even in the absence of solvent. But, a solvent may be used for the purpose of facilitating the control of the reaction temperature. The solvent for this purpose can be illustrated by n-pentane, n-octane, iso-octane, trichloroethane, tetrafluoroethane, etc. The appropriate amount of the solvent for use in effecting the reaction is in the range of ¼ – 2 times as much as the material olefin (by volume).

After completing the reaction, the polymerization product is subjected to distillation or extraction treatment by the conventional method thereby to separate the unreacted olefin and/or olefin dimer mixed in the polymerization product. And, in the case where it is desired to improve the oxidation stability and/or thermal stability of the product polyolefin oil, it can be easily effected by subjecting said polyolefin oil to hydrogenation treatment by the use of a typical hydrogenation catalyst such as Raney nickel, nickel on kieselguhr, etc.

As will be understood from the foregoing elucidation, according to the polymerization method of the present invention, it is possible to prevent halogen from mixing in the product polyolefin oil and obtain an olefin oligomer having low viscosity and high viscosity index at a high yield. As to the reason why such an excellent effect can be brought on in the present invention, as will be attested to by the comparison of examples embodying the present invention with reference examples to be shown later on, it is presumed that the three ingredients of the catalyst employed in the present invention manifest a unique synergetic effect, though their exact reaction mechanism is yet to be clarified.

DESCRIPTION OF THE PREFERRED EMBODIMENTS

After stocking aluminum chloride and metallic aluminum powder at various quantitative ratios such as shown in the following Table-I in a 1 l glass autoclave with stirrer, by adding polyhydric alcohol ester thereto while stirring, elevating the temperature up to 100° C and continuing the stirring for 3 hours, varieties of catalysts were prepared. Subsequently, by adding 600 g of material olefin to each of the thus obtained catalysts dropwise, polymerization was effected at 100° C for 5 hours. The kind and amount of the respective material olefin and polyhydric alcohol ester employed were as shown in Table-I. After completing the reaction, ammonia gas was blown into the polymerization product thereby to inactivate the catalyst and the thus separated catalyst was removed by filtration. Thereafter, the polymerization product was subjected to distillation to remove the unreacted olefin and olefin dimer therefrom, whereby a polyolefin oil was obtained respectively.

TABLE I

| Experiment No. | Olefin | (a)Polyhydric alcohol ester g | Aluminum chloride (b) g (molar ratio of b to a) | | Al powder (c) g (molar ratio of c to b) | |
|---|---|---|---|---|---|---|
| 1(Ref. Exper.) | octene-1 | ethylene glycol diacetate 6.6 g | 12 g | (1.0) | — | |
| 2*(Ref. Exper.) | " | — | " | ( — ) | 1.2 g | (0.5) |
| 3 | " | ethylene glycol diacetate 6.6 g | " | (1.0) | " | ( " ) |
| 4 | " | 1,3-diacetoxypropane 7.2 g | " | ( " ) | " | ( " ) |
| 5 | " | 1,4-diacetoxybutane 7.8 g | " | ( " ) | " | ( " ) |
| 6 | octene-1 | ethoxyethyl acetate 5.9 g | 12 g | (1.0) | 1.2 g | (0.5) |
| 7 | " | butoxypropyl acetate 7.8 g | " | ( " ) | " | ( " ) |
| 8 | " | ethoxyethoxyethyl acetate 5.3 g | " | ( " ) | " | ( " ) |
| 9 | " | ethylene glycol diacetate 8.2 g | " | (0.8) | " | ( " ) |
| 10 | " | ethylene glycol diacetate 9.4 g | " | (0.7) | " | ( " ) |
| 11(Ref. Exper.) | octene-1 | ethylene glycol diacetate 13.2 g | 12 g | (0.5) | 1.2 g | (0.5) |
| 12(Ref. Exper.) | olefin mixture | ethylene glycol diacetate 6.6 g | " | (1.0) | 0.12 g | (0.05) |
| 13 | " | ethylene glycol diacetate 6.6 g | " | (1.0) | 0.24 g | (0.1) |
| 14 | " | ethylene glycol diacetate 6.6 g | " | ( " ) | 1.94 g | (0.8) |
| 15 | " | ethylene glycol diacetate 6.6 g | " | ( " ) | 2.91 g | (1.2) |
| 16 | olefin mixture | ethylene glycol diacetate 6.6 g | 12 g | (1.0) | 7.28 g | (3.0) |

(Remarks)
1. Only in Experiment No. 2, the temperature for reaction was 180° C.
2. The bracketed Ref. Exper. stands for reference experiment.
3. The olefin mixture in Experiment Nos. 12–16 was a mixture composed of α-olefins having 6, 8 and 10 carbon atoms, respectively, at the molar ratio of 1:1:1.

The yield, viscosity and viscosity index of the polyolefin oil obtained in each experiment were as shown in the following Table-II.

And, when 500 g each of the respective polyolefin oils obtained in these experiments were subjected to 3 hours' hydrogenation treatment by applying a hydrogen pressure of 10 Kg/cm$^2$ and a temperature of 150° C in the presence of 15 g of Raney nickel catalyst and the bromine number of the resulting hydrogenated oil was measured, the result was as shown in Column-5 of Table-II.

Further, the amount of the halogen contained in the respective polyolefin oils was evaluated through the following procedure. First, the distillation apparatus used in removing the unreacted olefin and olefin dimer from the polymerization product was examined to confirm whether there was any corrosion thereof. The result of said examination was as shown in Column-6 of Table-II. The showings in Column-7 of Table-II are illlustrative of the frequency of repeated uses of one and the same catalyst for the foregoing hydrogenation treatment of polyolefin oil, coupled with the bromine number of the hydrogenated oil obtained on that occasion. As has already been explained, a polyolefin oil which can be turned into a hydrogenated oil having bromine number of less than 0.5 even by means of a catalyst serving for the tenth time of repeated use can be considered as simply free form halogen.

TABLE II

| | Properties of Polyolefin oils | | | | | |
|---|---|---|---|---|---|---|
| | Polyolefin oil | | | | | |
| Experiment No. | yield (%) | Kinematic viscosity at 100° F (centistoke) | Viscosity index (VIE) | Bromine number of hydrogenated oil | Corrosion of hydrogenation apparatus | Frequency of reuse and bromine number |
| 1 (Ref. Exper.) | 83 | 19.5 | 128 | 0.2 | some | 3 times; 3.0 |
| 2*(Ref. Exper.) | 77 | 32.5 | 105 | 0.3 | nil | no deterioration |
| 3 | 91 | 20.3 | 127 | 0.2 | " | 10 times; 0.3 |
| 4 | 90 | 19.1 | 128 | 0.2 | " | 10 times; 0.3 |
| 5 | 89 | 22.8 | 130 | 0.2 | " | 10 times; 0.3 |
| 6 | 94 | 41.5 | 132 | 0.2 | " | 10 times; 0.3 |
| 7 | 93 | 42.3 | 131 | 0.2 | nil | 10 times; 0.3 |
| 8 | 94 | 42.9 | 131 | 0.2 | " | 10 times; 0.3 |
| 9 | 88 | 19.9 | 128 | 0.2 | " | 10 times; 0.3 |
| 10 | 85 | 20.1 | 128 | 0.2 | " | 10 times; 0.3 |
| 11(Ref. Exper.) | 15 | 20.4 | 128 | 0.2 | " | 10 times; 0.3 |
| 12(Ref. Exper.) | 83 | 20.8 | 128 | 0.2 | some | 3 times; 3.5 |
| 13 | 90 | 20.5 | 128 | 0.2 | nil | 10 times; 0.5 |
| 14 | 91 | 20.4 | 128 | 0.2 | " | 10 times; 0.3 |
| 15 | 92 | 20.7 | 128 | 0.2 | nil | 10 times; 0.3 |

TABLE II-continued

| | | Properties of Polyolefin oils | | | | |
| | | Polyolefin oil | | | | |
| Experiment No. | yield (%) | Kinematic viscosity at 100° F (centistoke) | Viscosity index (VIE) | Bromine number of hydrogenated oil | Corrosion of hydrogenation apparatus | Frequency of reuse and bromine number |
|---|---|---|---|---|---|---|
| 16 | 94 | 20.9 | 128 | 0.2 | ″ | 10 times; 0.3 |

(Remarks)
1. Only in Experiment No. 2, the temperature for reaction was 180° C.
2. The bracketed Ref. Exper. stands for reference experiment.

What is claimed is:

1. A method of preparing an olefin oligomer by polymerizing an olefin or an olefin mixture having more than 6 carbon atoms, wherein said olefin or olefin mixture is to be polymerized in the presence of a catalyst mixture consisting of (a) polyhydric alcohol derivative obtained by substituting hydrogen atoms of the whole hydroxyl groups of polyhydric alcohol by either acyl group exclusively or acyl group and alkyl group, both said acyl group and alkyl group having 1 – 20 carbon atoms, (b) aluminum halide in an amount of 0.7 – 1.0 mole per each ester bond and ether bond possessed by said polyhydric alcohol derivative and (c) metallic aluminum powder.

2. A method according to claim 1, wherein the amount of metallic aluminum powder contained in said catalyst mixture is in the range of 2.7 – 135 g per 1 mole of aluminum halide.

3. A method according to claim 1, wherein said polyhydric alcohol derivative is selected from the group consisting of ethoxyethyl acetate, butoxypropyl acetate, ethoxyethoxyethyl acetate, ethylene glycol acetate, 1,3-diacetoxypropane and 1,4-diacetoxybutane.

4. A method according to claim 1, wherein said polyhydric alcohol derivative is mixed with aluminum halide and metallic aluminum powder, and to the resulting catalyst mixture is added said olefin.

5. A method according to claim 1, wherein said polymerization is effected in a solvent selected from the group consisting of n-pentane, n-octane, iso-octane, trichloroethane and tetrafluoroethane in an amount of 25 – 200% by volume, based on the olefin.

* * * * *